United States Patent
Kowalski et al.

(10) Patent No.: US 9,847,700 B2
(45) Date of Patent: Dec. 19, 2017

(54) MONITORING SYSTEM FOR AN ELECTRIC MACHINE

(71) Applicant: Siemens Aktiengesellschaft, Munich (DE)

(72) Inventors: Waldemar Kowalski, Mulheim an der Ruhr (DE); Christoph Lehmann, Neukirchen-Vluyn (DE)

(73) Assignee: Siemens Aktiengesellschaft, Munich (DE)

( * ) Notice: Subject to any disclaimer, the term of this patent is extended or adjusted under 35 U.S.C. 154(b) by 169 days.

(21) Appl. No.: 14/415,412

(22) PCT Filed: Jun. 11, 2013

(86) PCT No.: PCT/EP2013/061970
§ 371 (c)(1),
(2) Date: Jan. 16, 2015

(87) PCT Pub. No.: WO2014/016036
PCT Pub. Date: Jan. 30, 2014

(65) Prior Publication Data
US 2015/0200581 A1    Jul. 16, 2015

(30) Foreign Application Priority Data
Jul. 24, 2012    (EP) .................................... 12177578

(51) Int. Cl.
*H02K 11/00*    (2016.01)
*H02K 9/08*    (2006.01)
(Continued)

(52) U.S. Cl.
CPC ....... *H02K 11/001* (2013.01); *G01N 21/8803* (2013.01); *H02K 9/08* (2013.01);
(Continued)

(58) Field of Classification Search
CPC ........ H02K 11/001; H02K 11/20; H02K 9/08; H02K 15/00; G01N 21/8803
(Continued)

(56) References Cited

U.S. PATENT DOCUMENTS 4,962,660 A    10/1990 Dailey et al.
5,563,357 A * 10/1996 Longree ................... F16L 55/26
                                                                73/865.9

(Continued)

FOREIGN PATENT DOCUMENTS

CN    1081507 A    2/1994
CN    1148751 A    4/1997
(Continued)

OTHER PUBLICATIONS

English translation (machine translation) of JPH 10268390; Oct. 1998; Inoue et al.*

(Continued)

*Primary Examiner* — Bernard Rojas
*Assistant Examiner* — Ahmed Elnakib
(74) *Attorney, Agent, or Firm* — Beusse Wolter Sanks & Maire

(57) ABSTRACT

A monitoring system for monitoring an electric machine is provided. A mini-camera for observing the electric machine is arranged inside the electric machine. Moreover, the mini-camera is arranged movably on guide elements, wherein the guide element is designed in such a way that the mini-camera is held in an uncritical parked position during the operation of the electric machine.

10 Claims, 1 Drawing Sheet

(51) Int. Cl.
  *G01N 21/88* (2006.01)
  *H02K 15/00* (2006.01)
  *H02K 11/20* (2016.01)
  *G01R 31/34* (2006.01)

(52) U.S. Cl.
  CPC ............. *H02K 11/20* (2016.01); *H02K 15/00* (2013.01); *G01N 2201/061* (2013.01); *G01R 31/343* (2013.01)

(58) Field of Classification Search
  USPC .......... 310/55, 52, 58, 59, 68 R, 68 B, 68 C, 310/67 R; 73/866.5
  See application file for complete search history.

(56) References Cited

U.S. PATENT DOCUMENTS

| | | | |
|---|---|---|---|
| 5,650,579 A | 7/1997 | Hatley et al. | |
| 5,682,102 A * | 10/1997 | Takahashi | H02K 11/20 324/545 |
| 6,810,099 B2 | 10/2004 | Nakamaru et al. | |
| 7,555,966 B2 | 7/2009 | Hatley | |
| 8,308,354 B2 | 11/2012 | Watanabe et al. | |
| 8,410,623 B2 | 4/2013 | Stockner | |
| 8,431,917 B2 | 4/2013 | Wang et al. | |
| 8,498,826 B2 | 7/2013 | Nagathil et al. | |
| 8,869,637 B2 | 10/2014 | Zadeh et al. | |
| 2005/0116555 A1* | 6/2005 | Rowe | H02K 9/005 310/58 |
| 2007/0277629 A1 | 12/2007 | Hatley | |
| 2010/0135354 A1 | 6/2010 | Watanabe et al. | |
| 2011/0140419 A1 | 6/2011 | Stockner | |
| 2011/0226072 A1* | 9/2011 | Safari Zadeh | H02K 5/22 73/865.8 |

FOREIGN PATENT DOCUMENTS

| | | |
|---|---|---|
| CN | 201113619 Y | 9/2008 |
| CN | 101517872 A | 8/2009 |
| CN | 102539180 A | 7/2012 |
| DE | 202009015603 U1 | 4/2010 |
| EP | 1862381 A2 | 12/2007 |
| EP | 2261504 A1 | 12/2010 |
| JP | S5561258 A | 5/1980 |
| JP | S55061258 A | 5/1980 |
| JP | S57126055 U | 8/1982 |
| JP | S5930664 U | 2/1984 |
| JP | S62233793 A | 10/1987 |
| JP | H0332339 A | 2/1991 |
| JP | H07509311 A | 10/1995 |
| JP | H0998555 A | 4/1997 |
| JP | H09098555 A | 4/1997 |
| JP | H11248448 A | 9/1999 |
| JP | 2002122686 A | 4/2002 |
| JP | 2003271234 A | 9/2003 |
| JP | 2008044263 A1 | 4/2008 |
| JP | 2008109743 A | 5/2008 |
| JP | 2009159705 A | 7/2009 |
| JP | 2011200110 A | 10/2011 |
| JP | 2012118978 A | 6/2012 |
| JP | 2012133365 A | 7/2012 |
| WO | 9400738 A1 | 1/1994 |

OTHER PUBLICATIONS

CN Office Action dated Jun. 29, 2016, for CN application No. 201380039720.2.
JP Office Action dated Dec. 12, 2016, for JP patent application No. 2015-523465.
CN Office Action dated Nov. 8, 2016, for CN patent application No. 201380039720.2.
JP Notice of Allowance dated Jun. 12, 2017, for JP patent application No. 2015523465.

* cited by examiner

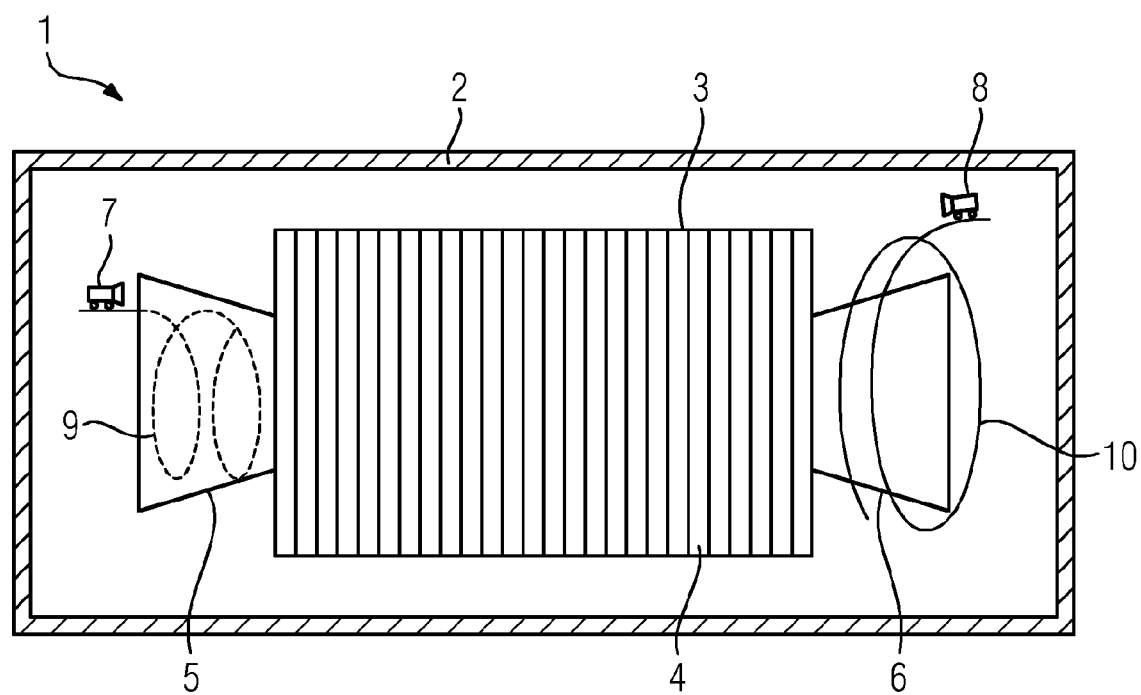

MONITORING SYSTEM FOR AN ELECTRIC MACHINE

CROSS REFERENCE TO RELATED APPLICATIONS

This application is the US National Stage of International Application No. PCT/EP2013/061970 filed Jun. 11, 2013, and claims the benefit thereof. The International Application claims the benefit of European Application No. EP12177578 filed Jul. 24, 2012. All of the applications are incorporated by reference herein in their entirety.

FIELD OF INVENTION

The invention relates to a monitoring system for monitoring an electric machine, wherein the electric machine has a housing and a stator winding comprising a stator end winding, which stator winding is arranged in the housing.

BACKGROUND OF INVENTION

Electric machines such as, for example, electric generators are formed substantially from a movable part, the rotor, and an immovable part, the stator. The rotor comprises a rotor winding, which substantially comprises large-volume copper lines which are supplied current for generating a magnetic field via an excitation device. The rotating magnetic field induces a voltage in electrically conductive stator windings arranged in a suitable manner on the stator. Generally, such electric generators are embodied in such a way that the electrical lines form a stator end winding at the ends of the stator winding.

During operation of an electric machine, various physical effects result in loading of the individual component parts. Thus, energy is firstly dissipated by an electrical resistance both in the stator winding and in the rotor winding, and this energy results in thermal loading of the individual component parts. Furthermore, the rotors are generally operated at comparatively high speeds such as, for example, 50 or 60 Hz, which results in enormous centrifugal forces and in mechanical loading. Such high speeds result not only in relatively high levels of loading in the rotor, but also in the stator, in particular in the stator end winding. The vibrations or oscillations associated with the rotation can shorten the life of electric generators with such a design.

Electric generators are generally cooled by air, hydrogen or water, depending on the electric power requirement. The cooling medium is guided in substantially hermetically sealed fashion in a housing in the electric generator, so that the housing is substantially gas-tight with respect to the surrounding environment.

In general, the generators are designed for continuous operation and are correspondingly used to capacity. During inspection work which is performed when the electric generator is at a standstill, the stator end windings are visually inspected by an inspector. For this purpose, access through an opening, for example through so-called manhole covers, is enabled, as a result of which a visual inspection is possible. Nevertheless, such spatial conditions are constricted in such a way that access to the stator end windings is only possible by partially dismantling further generator components, such as, for example, the end plate upper parts.

A further problem arises in that, in particular in the case of generators cooled by hydrogen, the cooling medium (hydrogen) needs to be flushed out of the interior of the electric generator, which involves considerable complexity. Even after supposedly successful blowout and flushing of the electric machine with inert gas, the electric machine still needs to be made safe before it can be inspected by formaldehyde and oxygen concentration measurements being performed.

It would be desirable to have an inspection possibility which means a lower level of complexity in comparison with the prior art.

SUMMARY OF INVENTION

An object of the invention therefore is to provide a monitoring system with which an electric machine can be inspected with a low level of complexity.

This object is achieved by a monitoring system for monitoring an electric machine, wherein the electric machine has a housing and a stator winding comprising a stator end winding, which stator winding is arranged in the housing, wherein a minicamera for observing the stator end winding is arranged within the housing.

Furthermore, this object is achieved by a method as claimed.

An essential concept of the invention includes arranging a suitable minicamera in the region of the stator end winding instead of opening the electric machine, which would mean considerable complexity. The minicamera is connected to an evaluation system by means of a suitable transmission possibility, either by means of wireless transmission or by means of wire-based transmission. The electric machine can therefore be monitored by an observer who is outside of the generator. The monitoring can therefore take place during operation.

Advantageous developments are specified in the dependent claims.

Thus, in a first advantageous development, the housing is substantially sealed in a gas-tight manner. Furthermore, advantageously the electric machine is embodied with hydrogen cooling. This means that the monitoring system according to the invention is particularly well suited to hydrogen-cooled generators, which in a known manner are particularly gas-tight. In a further advantageous development, the minicamera is embodied with a light source. This light source would need to have dimensions such that the view in onto the elements or components in the electric machine to be viewed which is necessary with the camera is guaranteed.

The minicamera is advantageously arranged movably on guide elements. These guide elements can be in the form of rails and are configured such that guidance of the camera can take place in such a way that the view in onto the critical elements or components to be viewed which is necessary is guaranteed.

Advantageously, the guide element is nonmagnetic. Furthermore, the guide rail is arranged in such a way that the camera is arranged in a safe and uncritical parked position during operation. This parked position is selected such that the voltage distances are adhered to and, in addition, the prevailing mechanical loading, such as, for example, cooling gas flows, is also taken into consideration. Therefore, the camera can be held in a safe position.

Advantageously, the guide element is guided in circular paths around the stator end winding.

The invention will now be explained in more detail below with reference to an exemplary embodiment.

BRIEF DESCRIPTION OF THE DRAWINGS

In the drawing:

FIG. 1 shows a schematic view of the monitoring system.

DETAILED DESCRIPTION OF INVENTION

FIG. 1 shows schematically an electric generator 1 as an embodiment of an electric machine. The electric generator 1 substantially comprises a generator housing 2, which is substantially sealed in a gas-tight manner. A rotor (not illustrated in any more detail) is arranged rotatably within the generator housing 2 and rotates substantially at 50 Hz or 60 Hz. A stator winding 3 and a laminate stack 4 are arranged around the rotor, and an electric voltage can be induced in said laminate stack 4. A first stator end winding 5 and a second stator end winding 6 are arranged at the respective ends of the stator winding 3. Both the first stator end winding 5 and the second stator end winding 6 have a tendency towards undesired vibrations during operation. In the worst case scenario, such vibrations can cause damage to the first stator end winding 5 and the second stator end winding 6.

The stator winding 3 is cooled with hydrogen, for example, within the generator housing 2 via cooling possibilities (not illustrated in any more detail). Therefore, the generator housing 2 is gas-tight. The monitoring system for monitoring the electric machine 1 comprises the electric machine 1 and the generator housing 2, wherein a stator winding is arranged in the generator housing 2, said stator winding comprising a stator end winding 5, 6. A minicamera 7, 8, which is designed to observe the electric machine 1, in particular the first stator end winding 5 and the second stator end winding 6, is arranged within the generator housing 2. The minicamera 7, 8 is embodied with a light source (not illustrated in any more detail) and is arranged movably on guide elements 9, 10. These guide elements 9, 10 are in the form of rails and are expediently nonmagnetic since the magnetic fields prevailing in the electric generator 1 could result in interference.

The guide elements 9, 10 are guided in circular paths around the first stator end winding 5 and around the second stator end winding 6.

In a manner which is not shown in any more detail, the guide elements 9, 10 are formed in such a way that, during operation of the electric machine 1, the minicamera 7, 8 is held in an uncritical parked position.

An advantage of the invention arises in that the electric generator 1 does not need to be opened or partially disassembled in the case of a visual inspection. Furthermore, the hydrogen-cooled electric generator 1 does not need to be subjected to blowout and pressure-tested again once closed. The inspection by the monitoring system according to the invention demonstrates improved quality by virtue of defined and constant observation of the components.

Furthermore, a considerable amount of time can be saved with the monitoring unit according to the invention. A resultant improved trend observation is thus possible. In addition, no replacement parts when the generator 1 is closed, for example seals or new screw elements, are required. The monitoring system is in this case designed in such a way that monitoring of the electric machine 1 is possible during operation.

The invention claimed is:

1. An electric machine comprising a monitoring system for monitoring the electric machine,
    wherein the electric machine comprises a generator housing, a stator, and a stator winding comprising a stator end winding, which stator winding is arranged in the generator housing,
    wherein a camera for observing the stator end winding is arranged within the generator housing,
    wherein the camera is arranged movably on a guide element, wherein the guide element is configured to hold the camera in a parked position inside the generator housing during operation of the electric machine,
    wherein the guide element comprises a spiral shaped guide rail, and
    wherein the spiral shaped guide rail is axially aligned with and radially outside of the stator end winding with respect to a longitudinal axis of the stator, effective to enable the camera to inspect a radially outer side of the stator end winding.

2. The electric machine as claimed in claim 1,
    wherein the monitoring system is configured so the stator end winding is observable during operation of the electric machine.

3. The electric machine as claimed in claim 1,
    wherein the generator housing is sealed in a gas-tight manner.

4. The electric machine as claimed in claim 1,
    wherein the electric machine is embodied with hydrogen cooling.

5. The electric machine as claimed in claim 1,
    wherein the camera is embodied with a light source.

6. The electric machine as claimed in claim 1,
    wherein the guide element is nonmagnetic.

7. The electric machine as claimed in claim 1,
    wherein the monitoring system is adapted for monitoring the electric machine in the form of an electric generator.

8. A method for monitoring a stator end winding of an electric machine, comprising:
    monitoring the stator end winding with the monitoring system as claimed in claim 1 during operation of the electric machine.

9. An electric machine, comprising:
    a generator housing; a stator; a stator winding comprising a stator end winding configured to extend past the stator; a camera; and
    a guide rail disposed within the generator housing and comprising a spiral shape, the guide rail configured to enable the camera to be in a parked position inside the generator housing during operation of the electric machine, and to enable the camera to be moved along the spiral shape about a longitudinal axis of the stator to inspect the stator end winding,
    wherein the spiral shape of the guide rail is axially aligned with and radially outside of the stator end winding with respect to the longitudinal axis of the stator, effective to enable the camera to inspect a radially outer side of the stator end winding.

10. The electric machine of claim 9, wherein in the parked position the camera does not axially overlap the stator winding with respect to the longitudinal axis of the stator.

* * * * *